US008461360B2

(12) United States Patent
Gokaraju et al.

(10) Patent No.: US 8,461,360 B2
(45) Date of Patent: Jun. 11, 2013

(54) PROCESS FOR PRODUCING γ-MANGOSTIN (75) Inventors: Ganga Raju Gokaraju, Vijayawada (IN); Rama Raju Gokaraju, Vijayawada (IN); Trimurtulu Golakoti, Vijayawada (IN); Venkateswarlu Somepalli, Vijayawada (IN); Kiran Bhupathiraju, Vijayawada (IN)

(73) Assignee: Laila Nutraceuticals, Vijayawada, IN (US)

( * ) Notice: Subject to any disclaimer, the term of this patent is extended or adjusted under 35 U.S.C. 154(b) by 241 days.

(21) Appl. No.: 12/863,514

(22) PCT Filed: Jul. 17, 2008

(86) PCT No.: PCT/IN2008/000460
§ 371 (c)(1),
(2), (4) Date: Jul. 19, 2010

(87) PCT Pub. No.: WO2009/093259
PCT Pub. Date: Jul. 30, 2009

(65) Prior Publication Data
US 2010/0292490 A1    Nov. 18, 2010

(30) Foreign Application Priority Data
Jan. 21, 2008  (WO) ................. PCT/IN2008/000040

(51) Int. Cl.
*C07D 311/86*  (2006.01)

(52) U.S. Cl.
USPC ....................................................... 549/392

(58) Field of Classification Search
USPC ................................. 549/391, 392
See application file for complete search history.

(56) References Cited

FOREIGN PATENT DOCUMENTS

| JP | 08225783 | 9/1996 |
| JP | 2005298379 | 10/2005 |
| WO | 2006137139 | 12/2006 |
| WO | 2007002666 | 4/2007 |
| WO | 2009093255 | 7/2009 |

OTHER PUBLICATIONS

Nutritional Business Journal, 2006, pp. 186-200.
Nakatani et al., Inhibition of cyclooxygenase and prostaglandin E2 sythesis by gamma-mangostine, a xanthone derivative of mangosteen, in C6 rat glioma cells. Biochem. Pharmacol, V63: pp. 73-79, 2002.
Nakatani et al., Gamma-Mangostin Inhibits Ihibitor-KB Kinase Activity and Cecreases Lipopolysacchariede-Induced Cyclooxygenase-2 Gene Expression in C6 Rat Glioma Cells, Molecular Pharmacol 66: 667-674, 2004.
Mahabusarakam, W., et al., Chemical Constituents of *Garcinia mangostana*, J. Natural Products, 50, pp. 474-478, 1987.
Govindacahri, T.R. et al. Xanthones of *Garcinia mangostana* Linn, Tetrahedron, vol. 27, pp. 3919-3926, 1971.
Jefferson et al., Studies in the Xanthone Series XVIII. Isolation of Gamma mangostin from *Garcinia mangostana* and Preparation of the Natural Mangostins by Selective Demetylation, Australian J. Chemistry, 23, pp. 2359-43, 1970.
Yates et al., The Structure of Mangostin, J. Am Chem. Soc., 1958, 80(7), pp. 1691-1700.
Akiyama et al., AlC13-N, N-Dimethylaniline: A New Benzyl and Allyl Ether Cleavage Reagent. Tetrahedrom Letters, vol. 32, No. 10, pp. 1321, 1991.
Akiyama et al., AlC13-N, N-Dimetheylaniline: A Novel Benzyl and Allyl Ether Cleavage Reagent, Bull. Chem Soc. Japan, 65, pp. 1932-1938 (1994).
Lange, R. G., Cleavage of Alkyl o-Hydroxyphenyl Ethers, Journal of Organic Chemistry, 1962, vol. 27, pp. 2037-2039.
Schmid et al., Demethylation of 4-Methoxyphenylbutyric Acid Using Molten Pyridinium Hydrocholoride on Multikilogram Scale. Organic Process Research & Development 2004, 8, pp. 670-673.
Schewe et al., Enxymology and Physiology of Reticulocyte Lipoxygenase: Comparison with Other Lipoxygenases, Adv Enzymol, vol. 58: pp. 191-272 (1986).
Reddanna et al., Purification of Arachidonate 5-Lipoxygenase for Potato Tubers, Biosynthesis, Enzymology and Chemical Synthesis, Methods in Enzymology, vol. 187, pp. 268-277, 1990.

*Primary Examiner* — Bernard Dentz
(74) *Attorney, Agent, or Firm* — Kramer Amado, P.C.

(57) ABSTRACT

A process for the production of γ-mangostin comprising the steps of preparing O-methyl γ-mangostin preferably from plants, subjecting the pure or partially pure O-methylated γ-mangostin to demethylation reaction procedure followed by purification of the said demethylated product to obtain pure γ-mangostin.

25 Claims, 5 Drawing Sheets

PROCESS FOR PRODUCING γ-MANGOSTIN

RELATED APPLICATION

This application claims priority from our earlier PCT International Application No. PCT/IN08/0000040 dated 21 Jan. 2008; the contents of which are incorporated herein in its entirety.

FIELD OF THE INVENTION

This invention relates to a process for the production of γ-mangostin, which comprises, preparing O-methyl γ-mangostin preferably from plants, subjecting the pure or partially pure O-methyl γ-mangostin to demethylation reaction followed by purification of the said demethylated product to obtain pure γ-mangostin.

BACKGROUND OF THE INVENTION

Xanthones are a large group of secondary metabolites found in a wide variety of plants. The substitution pattern on the xanthone backbone varies depending upon the nature of the plant source. Mangostins are active principles isolated from *Garcinia mangostana* L, also known as mangos teen, of the Guttiferace family, which are responsible for mangosteen's anti-inflammatory and many other biological properties. The fruit hull of *G. mangostana* has been used as a traditional medicine in Southeast Asia for the treatment of diarrhea, inflammation, and ulcers. Mangos teen has been highly popular for their perceived role in enhancing human health (U.S. Pat. No. 6,730,333 B1). The fruit juice made of mangos teen has become a major botanical dietary supplement, and was ranked as one of the top-selling "botanicals" in the Food, beverage & supplement market in 2005 (Nutritional Business Journal, 2006, pp. 186-200). α-Mangostin (2) is the most prominent among more than a dozen xanthone compounds exist in mangos teen. γ-Mangostin, whose structure was deduced as 2,8-bis[(2E)-3-methyl but-2-only)-1,3,6,7-tetrahydroxyxanthen-9-one (1) based on chemical and spectroscopic analysis (Journal of American Chemical Society, 1958, Vol. 80, pp. 1691-1700), is a minor metabolite.

The mangostin compounds were found to inhibit both 5-lipoxygenase and cycloxygenase-2 enzymes (Nakatani, K., et. al., Biochem. Pharmacol, V63: pp 73-79, 2002). γ-Mangostin directly inhibits IKK activity, which specifically phosphorylates IκB, and thereby prevents its degradation and, as a result, induces a decrease in the expression of COX-2 protein and its mRNA by a suppression of NF-κB-dependent transcription. (Nakatani, K., et. al., Biochem. Pharmacol., V66: pp 667-674, 2002).

Despite the established broad spectrum pharmacological activities and long history of usage of the extracts having γ-mangostin, its occurrence in *G. mangostana* fruit extract is very low and its availability is very limited due to the lack of cost viable processes.

The US patent application 20060014967 relates to a process for obtaining and purifying pure α-mangostin from the rind of the fruit (mangos teen) of *Garcinia mangostana*.

WO06137139A1 provide a method of isolating a mangos teen derivative whereby the mangos teen derivative having various pharmacological effects can be efficiently purified by using a highly safe solvent, and a drug and a health food containing the mangos teen derivative having a high safety.

JP2005298379A2 describe an IκB kinase inhibitor inhibiting IκB kinase (a) causing NF-κB activation causing transcriptional enhancement of genes relating to immunity, inflammatory reaction, cell growth control and apoptosis, comprising at least one selected from extracts, extracted from fruits or pericarps of a mangos teen (*Garcinia mangostana* L.), α-mangostin and γ-mangostin is provided, and a composition containing the inhibitor is provided.

JP08225783A2 describes an antioxidant containing an extract separated from the pericarp of a mangos teen as an active ingredient. The active ingredient is obtained by pulverizing the dried mangos teen, then carrying out the cold leaching with methanol, subsequently partitioning and extracting the methanol extraction essence with acetic acid and water at 1:1 ratio, then treating a part passed into the ethyl acetate by a silica gel chromatography, eluting the resultant extract with n-hexane-ethyl acetate (at 3:1 ratio) and thereby providing the extract as a fraction containing γ-mangostin of the formula.

WO07002666A2, US20060292255A1 and US20060105069A1 relates to pharmaceutical, therapeutic, nutritional, cosmetic, and dermatological compositions derived from the pericarp (rind) of the *Garcinia mangostana* L plant and the extraction processes used to produce those compositions. This patent application describes compositions comprising an approximately 0.01% to about 80% mixture of a xanthone-rich mangos teen pericarp (rind) extract in novel combinations for pharmaceutical, cosmetic, therapeutic or dermatological compositions that yield surprising health benefits.

All the process patents described above relates to general enrichment of total spectrum of mangostin compounds exist in the *Garcinia mangostana* fruit pericarp. The specification of the above patent US20060292255A1 though claims inadvertently the enrichment of γ-mangostin upto 40%, no such selective enrichment of γ-mangostin has been attempted or described. The process described therein, which involves merely a base treatment and partitions, could not have achieved the selective enrichment of γ-mangostin over α-mangostin as the physical and chemical properties of the γ-mangostin and α-mangostin are closely similar.

Enriching the γ-mangostin to phytochemical purity from its 3-5% natural abundance commonly exist in the extract, through a process involving column chromatography, as described in patent JP08225783A2 for identification and bioactivity study purposes is not economical for bulk enrichment or commercial utility.

None of the prior art relates to the selective enrichment of γ-mangostin from the natural mangostin extracts derived from *Garcinia mangostana*. Hence, there exists a need for extracts that offers the health benefits of *Garcinia mangostana* and comprise prominently and highly enriched in γ-mangostin.

It is, therefore, an object of the present invention to provide a process for producing extracts highly enriched in γ-mangostin and to produce γ-mangostin up to 99% using a commercially viable process.

SUMMARY OF THE INVENTION

The present invention discloses the practical process for the production of γ-mangostin from O-methylxanthone or mixtures containing O-methylxanthones having the general formula I.

General formula I

Wherein $R_1$, $R_2$, $R_3$ and $R_4$ may be H or $CH_3$

The invention discloses the process for the production of γ-mangostin from O-methylxanthone or mixtures containing O-methylxanthones having the general formula I by using demethylating reagent such as aluminum chloride in the presence of organic amine and a catalyst such as potassium iodide. The O-methylxanthones as shown in general formula I or their mixtures are in the form of crude extract or pure compounds preferably from the plants that produce compounds of the general formula I, such as *Garcinia mangostana* L, *Garcinia* cowa, *Cratoxylum cochinchinense*, *Garcinia* dulcis or *Garcinia* fusca.

Improved process for manufacturing of γ-mangostin over the general reference and description in our earlier PCT International Application No. PCT/IN08/0000040, which is referred to herein as priority, is described more specifically herein with specific preferred embodiments.

DETAILED DESCRIPTION OF THE INVENTION

The inventors performed some antioxidant activity studies on mangostins to compare the activity and found that γ-mangostin possesses more potent antioxidant activity compared to α-mangostin. The inventors have also conducted several enzymatic and cell based in vitro studies and found that γ-mangostin is superior inhibitor of inflammatory markers such as 5-lipoxygenase enzyme and aP2 (Adipocyte fatty acid binding protein) when compared to the major xanthone α-mangostin. The above in vitro efficacy data is further supported by the better efficacy shown by γ-mangostin (37%) when compared to α-mangostin (23%) in reducing paw edema in Freund Complete Adjuvant (FCA) induced arthritis model of Sprague Dawley rats.

Hence, the foregoing suggests that γ-mangostin or the extracts or compositions abundant in γ-mangostin are more desirable therapeutically. However, its low abundance in *G. mangostana*, limits γ-mangostin's usage to exploratory studies only, and quantities needed for commercial application are not available presently.

The process for the preparation of pure γ-mangostin or extracts/compositions selectively enriched in γ-mangostin was not attempted in the prior art thus far, except a conventional purification of minor quantity of γ-mangostin that is naturally exists in the extracts by laborious column chromatography procedure. More importantly, a cost effective and commercially viable process for bulk production of 99% γ-mangostin has not been disclosed. These lacunas, which were not addressed by any prior art patents or literature articles, have been the subject matter of the present invention. Hence, the main objective of the present invention is to develop a process for producing γ-mangostin.

The great diversity of the molecular architecture in γ-mangostin has made it a challenging target for synthesis and biological evaluation. A synthetic route for the lab scale preparation of γ-mangostin has not been reported. A synthetic process for commercial scale production of γ-mangostin is not easily accessible due to the requirement for large number of process steps and some expensive reagents. As the source of γ-mangostin has been significantly low in *G. mangostana* for commercial purification, the inventors have screened more than 100 plant extracts using HPLC method of analysis for an alternate source of γ-mangostin. None of the extracts showed detectable levels of γ-mangostin. However, the inventors found that O-methylxanthones of the general formula-I, have been highly abundant in many plant extracts as detailed below.

The methanol extract of *Garcinia mangostana* fruit, for example has been found to be a rich source containing up to 35% wt. of α-mangostin, a 7-O-methyl γ-mangostin (2). The other sources of α-mangostin are *Allanblackia monticola*, *Cratoxylum cochinchinense*, *Garcinia* cowa, *Garcinia* dulcis and *Garcinia* fusca. The α-mangostin has been purified from the crude extract of *Garcinia mangostana* and its chemical structure has been deduced based on its chemical and physical characteristics and by comparison with the spectroscopic data reported in literature as 2,8-bis[(2E)-3-methyl but-2-only)-1, 3,6-trihydroxy-7-methoxyxanthen-9-one (2).

The β-mangostin, a 3,7-di-O-methyl γ-mangostin has been found to occur in *Allanblackia monticola*, *Cratoxylum cochinchinense*, *Garcinia* cowa, *Garcinia* dulcis and *Garcinia* fusca. The crude extract from *Garcinia* cowa has been purified to get pure β-mangostin. There has been some confusion over the chemical structure of β-mangostin in the prior art documents. Mahabusarakam, W., et. al., reported the structure of β-mangostin as 3 (J. Natural Products, 50, pp 474-78, 1987), where as Govindachari, T. R., et. al. has reported its structure as 7 (Tetrahedron, 27, pp 3919-26, 1971). The inventors have now confirmed its chemical structure based on its chemical and physical characteristics and by comparison with the spectroscopic data reported in literature as 2,8-bis[(2E)-3-methyl but-2-only)-1,6-dihydroxy-3,7-dimethoxyxanthen-9-one (3).

The 6,7-di-O-methyl γ-mangostin also called 2,8-bis[(2E)-3-methyl but-2-only)-1,3-dihydroxy-6,7-dimethoxyxanthen-9-one (4) and 3,6,7-trimethyl γ-mangostin also called 2,8-bis[(2E)-3-methyl but-2-only)-1-hydroxy-3,6,7-trimethoxyxanthen-9-one (5) have been found in *Garcinia* cowa and the latter has also been found in *Garcinia* fusca. The 3-O-methyl γ-mangostin also known as 2,8-bis[(2E)-3-methyl but-2-only)-1,6,7-trihydroxy-3-methoxyxanthen-9-one (6) has been found to occur in *Garcinia* dulcis as a minor metabolite.

Encouraged by the results of exploratory studies, which have manifested O-methyl γ-mangostins very prominently in many plant species, the inventors conceived an idea to produce γ-mangostin from O-methyl γ-mangostins by applying a chemical process called O-demethylation.

The prior art article communicated by Jefferson A., et. al., (Australian J. Chemistry, 23, pp 2539-43, 1970) provides a method for making γ-mangostin through demethylation of α-mangostin using large excess of morpholine (≈6 mL/g) in water medium in a steel bomb. The said method will have limited utility for commercial scale production as it requires steel bomb for execution. The elevated temperatures (140° C.) and very long reaction times (7 days) required for above method further limits the commercial viability of the method. Besides, the yield of γ-mangostin from the above procedure is only 62%, which makes it economically unviable due to higher cost of the starting compounds and reagents. In addition to the above, the contents of this article did not suggest the scope or utility of the method for impure starting material such as α-mangostin in a crude extract or partially purified extract. This is important as possibility to carry out the demethylation on plant extracts or partially purified fractions will have added process advantage.

Surprisingly, no other O-demethylation procedures have been known for the preparation of γ-mangostin from α-mangostin or from any other O-methyl xanthones related to γ-mangostin. Hence the inventors have experimented with many demethylation reaction procedures and the details of these procedures are described below.

Figure 1:
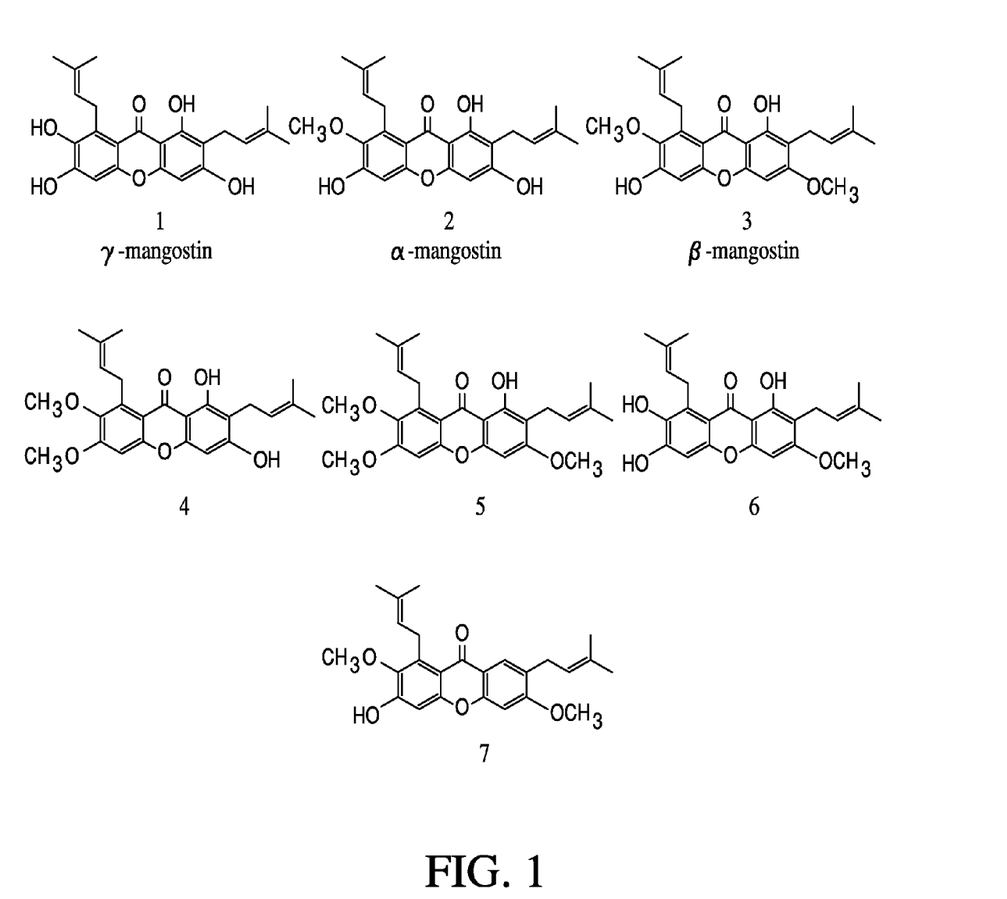
FIG. 1 presents the chemical structures of major xanthones isolated and characterized from *Garcinia mangostana* and other plants.
Figure 2:
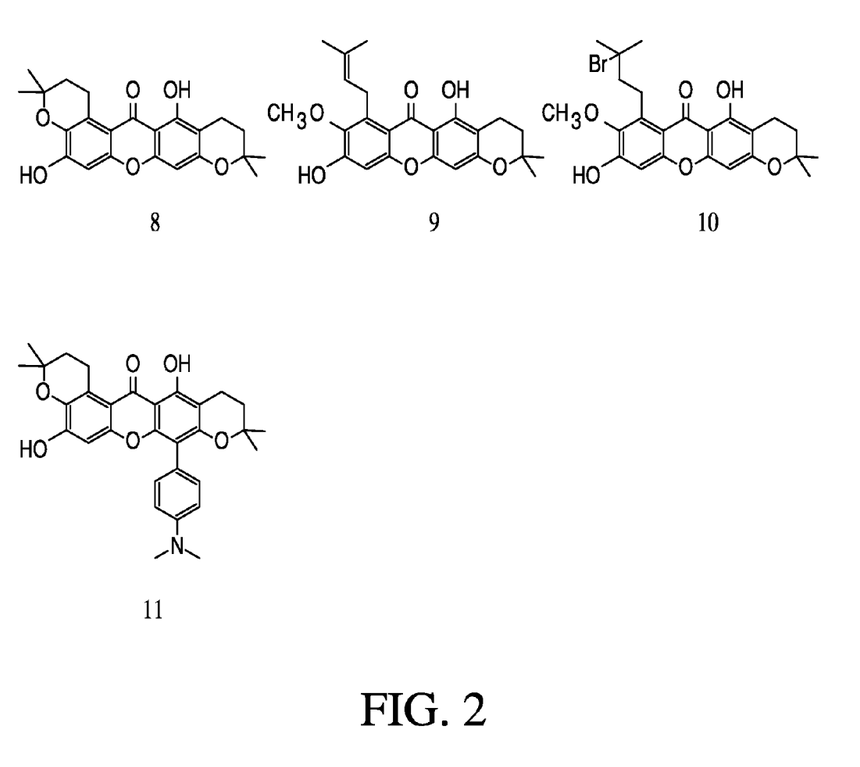
FIG. 2 presents the chemical structures of unwanted prenyl cyclized xanthones produced from demethylation reaction.

A demethylation procedure mediated by mineral acid such as sulfuric acid was randomly chosen for the first attempt. The α-mangostin was treated with conc. sulfuric acid or hydrobromic acid either at room temperature or higher temperatures. Extensive decomposition has taken place during the conversion process and unwanted side products were formed in significant quantities but no trace of γ-mangostin in either of these two reactions. The products of the HBr mediated conversion (example #5) were separated and characterized as 1,6-dihydroxy-6',6'-dimethyldihydropyrano (2',3':3,2)-6'',6''-dimethyldihydropyrano (2'',3'':7,8)xanthone (8, 21%), 1,6-dihydroxy-7-methoxy-8-(3-methyl-but-2-only)-6',6'-dimethyldihydropyrano-(2'3':3,2)xanthone (9, 15%) and 1,6-dihydroxy-8-(3-bromo-3-methyl-buty)-7-methoxy-6',6'-dimethyldihydropyrano-(2',3':3,2)xanthone (10, 16%) as depicted in figure 2. Similarly, the products of $H_2SO_4$ mediated reaction were identified as dimethyldihydropyrano xanthones 8 (24%) and 9 (10%). This confirms the similar result previous reported by Yates, P., wherein treatment of α-mangostin with hydroiodoic acid (HI) produced a dicyclized compound identical in all respects with 8 (Journal of American Chemical Society, 1958, Vol. 80, pp. 1691-1700).

For the next attempt the inventors opted for Lewis acids, for example $AlCl_3$ $AlBr_3$ etc., which are commonly employed for O-demethylation of aromatic compounds. The α-mangostin dissolved in 1,2-dichloroethane was treated with $AlCl_3$ (example #6). The TLC monitoring showed extensive decomposition. The work-up followed by purification did not show γ-mangostin in detectable quantities, but yielded unwanted by products 1,6-dihydroxy-7-methoxy-8-(3-methyl-but-2-only)-6',6'-dimethyldihydropyrano-(2',3':3,2)xanthone (9, 50%) when the reaction was conducted at RT, whereas cyclized products 8 (27%) and 9 (7%) were obtained at 80° C. temperature (example #7).

The inventors selected a procedure employed by Akiyama, T., et. al., for the O-debenzylation and O-deallylation of aromatic compounds (Tetrahedron Lett, p 1321, 1991; Bull. Chem. Soc. Jpn, 65, p1932, 1992), which was subsequently employed by Majeed, M. et. al., (U.S. Pat. No. 7,253,324 B1, dated Aug. 7, 2007) for the O-demethylation of aromatic compounds. As per the procedure described for O-methyl resveratrol, anhydrous aluminum chloride was added slowly under stirring at room temperature to N,N-dimethylaniline (example #8). After the addition is over dry toluene was added to the mixture and stirred for 15 min. The toluene solution of O-methylated aromatic compound to be demethylated was dropped to the above mixture under stirring and the mixture then heated at 100-110° C. for 2-3 h. After completion of the reaction, the mixture was cooled to room temperature and slowly poured into ice water with stirring and the mixture was acidified with HCl to pH=1-2. The toluene layer was separated and the aqueous layer extracted twice with toluene. The combined organic layer was extracted 10% aqueous sodium hydroxide and the basic phase acidified with HCl and extracted thrice with toluene. The toluene layer was dried over anhydrous sodium sulfate, filtered and the solvent stripped off under vacuum to obtain the demethylated compound. The execution of said reaction protocol on α-mangostin led prominently to the prenyl cyclized product (8, 52%), and an unexpected substitution product 11 (3%). Surprisingly, no trace of γ-mangostin was observed even after careful purification of the crude reaction product on silica column.

Lange, R. G. (Journal of Organic Chemistry, 1962, 27, pp. 2037) disclosed a modified procedure selectively for compounds possessing a free phenolic group ortho to the O-methyl group using aluminum chloride/pyridine/dichloroethane system. As per the given protocol, an ice cold solution of aromatic methyl ether in 1,2-dichloroethane is treated first with anhydrous $AlCl_3$. After stirring the mixture for 15 min, pyridine is added drop wise to the reaction mixture under brisk stirring while maintaining the temperature at 30-35° C. and then subjected the mixture to reflux for 24 h. After completion of the reaction, the reaction mixture is poured into cold dil. HCl and extracted either with chloroform or ethyl acetate. The organic solvent was dried over sodium sulfate and evaporated under vacuum. Purification of the residue either by column chromatography or crystallization gives demethylated product in good yield.

The inventors of the present application adopted the said reaction procedure for the demethylation of α-mangostin (example #9). The workup followed by purification as per the description given in the said prior art led to very low yield of γ-mangostin (3%) due the extensive decomposition of α-mangostin and/or demethylation followed by cyclization to 1,6-dihydroxy-6',6'-dimethyldihydropyrano(2',3':3,2)-6'',6''-dimethyl-dihydropyrano(2'',3'':7,8)xanthone (8, 40%).

The inventors also explored other types of demethylating agents. Pyridine-hydrochloride salt for example is prominently used for demethylation (Schmid, C. R., et. al., Organic Process Research & Development, 8, pp 670-673, 2004) and known to be relatively mild agent compared to Lewis acids. A mixture of α-mangostin and pyridine-hydrochloride salt was heated to 190-200° C. for 2 h (example # 10). At lower temperature no transformation occurred. The mixture was poured into water and extracted with ethyl acetate. The residue was purified by column chromatography and characterized to be dicyclized product (8, 62%). It is possible that the formation of 8 may have been the result of thermal cyclization.

Other O-demethylating agents like $NiCl_2$—Zn/xylene, $TiCl_4$—$BF_3$—KI, $CeCl_3$—NMP/acetonitrile, methane sulphonic acid, polyphosphoric acid and ionic liquids etc., have also led to decomposition and cyclized dimethyldihydropyrano xanthones but no trace of γ-mangostin.

Mangostin compounds have unique structure with very sensitive functional groups. Its xanthone main frame is uniquely equipped with four oxygen functionalities on C-1, C-3, C-6 and C-7 positions and two sensitive prenyl groups on C-2 and C-8 positions. The said xanthone system is highly labile to both mineral acids and Lewis acids, which leads to decomposition and the cyclization of the iso-prenyl moiety through the assistance of adjacent phenolic function to yield dimethyldihydropyrano xanthone(s), such as 1,6-dihydroxy-6',6'-dimethyldihydropyrano(2',3':3,2) xanthone-6",6"-dimethyldihydropyrano(2",3":7,8)xanthone (8) and/or 1,6-dihydroxy-7-methoxy-8-(3-methyl-but-2-only)-6',6'-dimethyldihydropyrano-(2',3':3,2)xanthone (9) as by-products, when the demethylation was attempted on α-mangostin or other O-methylxanthones of the general formula I.

Hence, it is the objective of the present invention to produce γ-mangostin efficiently and cost effectively through a process 1. that can be conducted at the atmospheric pressure
2. that can be conducted at an optimum temperature range
3. that has the small reaction time
4. that offers yields compatible to an economic process
5. that has the feasibility to scale-up for commercial volumes
6. and most importantly, a process that can effectively prevent the cyclization of the prenyl moieties in starting xanthones to dimethyldihydropyrano moieties in the product xanthones.

The latter objective is utmost important and crucial, as the unwanted cyclization is mostly responsible for the total absence or meager yield of γ-mangostin in the reaction products.

The inventors have thus conducted many experiments by randomly altering reagents, process steps and the reaction conditions and found unexpectedly that the decomposition and formation of the by-products can be reduced completely, and near quantitative yields can be obtained by adopting a unique reaction protocol as outlined below for the O-demethylation of α-mangostin to obtain γ-mangostin.

Step 1: preparation of pure, semi pure or mixtures of O-methyl xanthones of the general formula I, preferably from one of the plant source selected from *Garcinia mangostana, Garcinia cowa, Garcinia dulcis, Garcinia fusca, Garcinia speciosa, Hydnocarpus* species, *Cratoxylum formosum, Allanblackia monticola, Cratoxylum cochinchinense* and then subjecting the di and tri-O-methylxanthones of the general formula I to demethylation to produce α-mangostin.

Step 2: dissolving α-mangostin or an extract containing α-mangostin in an organic solvent, preferably 1,2-dichloroethane;

Step 3: treating the solution with an organic base and stabilize the solution for suitable period of time;

Step 4: treating the said xanthone mixture with Lewis acid and optionally with a catalyst at room temperature, followed by refluxing the reaction for a suitable period of time, until α-mangostin is totally converted to γ-mangostin;

Step 5: quenching the reaction by pouring into a mixture of ice water, an acid, preferably 3N HCl and brine.

Step 6: extracting the said acidified mixture with an organic solvent, preferably ethyl acetate or tetrahydrofuran or mixtures thereof and drying the organic layer with a drying agent;

Step 7: adding an organic base, preferably triethyl amine to the organic layer prior to evaporation of the solvent under vacuum to yield γ-mangostin;

Step 8: purifying the product to 99% purity by subjecting the said product to column chromatography or crystallization or both.

The step 3, comprising the addition of organic base to a solution of the O-methyl xanthone prior to the addition of the Lewis acid, and step 7, comprising the addition of organic base to solution containing γ-mangostin prior to the evaporation of the solvent, are unexpected and crucial to the success of the process.

The organic base (pyridine) was used in step 3, to neutralize the HCl generated during the reaction. Again an organic base was used in step 7 to prevent the formation of unwanted cyclized and addition products due to the traces of acid during the evaporation of the solvent at elevated temperature.

The said inventive process significantly reduced the reaction time and temperature needed for achieving the intended conversion. The inventive process can be conveniently performed at the atmospheric pressure. Very surprisingly, the above inventive procedure completely prevents the cyclization of the iso-prenyl moiety to dimethyldihydropyran moiety. The data from the trial reactions (examples 5 to 11) conducted with various known reagents and processes has been summarized in table 1 along with the similar data obtained from the inventive procedure (example 12). The γ-mangostin was totally absent or very low (≦2%) in all these trial reactions based on the prior art literature, whereas the yields of the unwanted cyclized products have been prominent and various from 34 to 62% in the trial experiments conducted with the known reagents and processes. Surprisingly, the inventive process has produced γ-mangostin in excellent yield (90%) and completely prevented the formation of the cyclized products, 8 and 9 as indicated by analysis of the demethylated product from pure α-mangostin.

O-Methyl γ-mangostins such as β-mangostin, 3-O-methyl-γ-mangostin, 6,7-dimethyl-γ-mangostin and 3,6,7-trimethyl-γ-mangostin are conveniently converted to α-mangostin first by demethylation using sodium cyanide (NaCN) in dimethyl sulfoxide (DMSO) and then subjected to inventive O-demethylation process to obtain γ-mangostin in good yield and high purity.

Hence the present invention relates to the practical process for the production of γ-mangostin from O-methyl xanthones or mixtures containing O-methyl xanthones having the general formula I.

TABLE 1

SUMMARY OF DEMETHYLATIONS ON α-MANGOSTIN

| Exa. # | Reagents and conditions | Product Structure # | Yield |
|---|---|---|---|
| 5 | α-mangostin + AcOH; HBr | 1 | 0% |
|  |  | 8 | 21% |
|  |  | 9 | 15% |
|  |  | 10 | 16% |
| 6 | α-mangostin + ClCH$_2$CH$_2$Cl; AlCl$_3$/RT | 1 | 0% |
|  |  | 9 | 50% |

TABLE 1-continued

SUMMARY OF DEMETHYLATIONS ON α-MANGOSTIN

| Exa. # | Reagents and conditions | Product Structure # | Yield |
|---|---|---|---|
| 7 | α-mangostin + ClCH$_2$CH$_2$Cl; AlCl$_3$/80° C. | 1 | 0% |
|   |   | 8 | 27% |
|   |   | 9 | 7% |
| 8 | N,N-DMA-AlCl$_3$/toluene; α-mangostin/toluene | 1 | 0% |
|   |   | 8 | 52% |
|   |   | 11 | 3% |
| 9 | AlCl$_3$/ClCH$_2$CH$_2$Cl; Pyridine | 1 | 3% |
|   |   | 8 | 40% |
| 10 | Pyridine-HCl/190-200° C. | 1 | 0% |
|   |   | 8 | 62% |
| 11 | α-mangostin + CH$_3$CN/CeCl$_3$—KI | 1 | 0% |
|   |   | 8 | 44% |
|   |   | 9 | 17% |
| 12 | α-mangostin + ClCH$_2$CH$_2$Cl + pyridine; AlCl$_3$ | 1 | 90% |
|   |   | 8 | 0% |

General Formula I

Wherein R$_1$, R$_2$, R$_3$ and R$_4$ may be H or CH$_3$

The preferred O-methyl xanthones of the general formula I for conversion to γ-mangostin are 2: 1,3,6-trihydroxy-7-methoxy-2,8-bis-(3-methyl-but-2-only) -xanthen-9-one α-mangostin, R$_1$=R$_2$=R$_3$=H; R$_4$=CH$_3$)

3: 1,6-dihydroxy-3,7-dimethoxy-2,8-bis-(3-methyl-but-2-only) -xanthen-9-one (β-mangostin, R$_1$=R$_3$=H; R$_2$=R$_4$=CH$_3$)

4: 1,3-dihydroxy-6,7-dimethoxy-2,8-bis-(3-methyl-but-2-only) -xanthen-9-one (R$_1$=R$_2$=H; R$_3$=R$_4$=CH$_3$)

5: 1-hydroxy-3,6,7-trimethoxy-2,8-bis-(3-methyl-but-2-only) -xanthen-9-one (R$_1$=H; R$_2$=R$_3$=R$_4$=CH$_3$)

6: 1,6,7-trihydroxy-3-methoxy-2,8-bis-(3-methyl-but-2-only) -xanthen-9-one (R$_1$=R$_3$=R$_4$=H; R$_2$=CH$_3$)

or mixtures thereof.

Organic solvent for conducting the demethylation reaction in step 2 is selected from chloroform, dichloromethane, 1,2-dichloroethane, 1,3-dicholropropane and ethyl acetate or mixtures thereof.

The organic base used for O-demethylation in step 3, is selected from the group consisting of pyridine, triethylamine, piperidine, N,N-dimethylaniline, N,N-diethylaniline and the like.

The Lewis acid used in step 4 is selected from a group consisting of aluminum chloride, aluminum bromide, aluminum iodide, boron tribromide, boron trichloride-methyl sulfide complex, boron trichloride, broron trifluoride, zinc chloride or iron chloride.

The catalyst used in step 4 is selected from metal iodide or PTC catalyst such as tetrabutylammonium bromide. The metal iodide is selected from a group comprising sodium iodide, potassium iodide, magnesium iodide, calcium iodide and the like.

The organic base used in step 7 is selected from triethylamine, tri-n-propyl amine, triisopropylamine, pyridine, N,N-dimethylaniline, N,N-diethylaniline and the like.

The chromatography used in step 8 may comprise a solid phase selected from one of ion exchange resins, Sephadex LH-20 gel, any synthetic adsorbent resin, normal phase silica, reversed phase silica etc. The solvent for the resin elution may be selected from hexane, ethyl acetate, chloroform, acetone, methanol, ethanol, n-propanol, isopropanol, n-butanol, isobutanol, water etc., or mixtures thereof.

The solvent for crystallization in step 8 is selected from the group consisting of hexane, dichloromethane, ethyl acetate, chloroform, acetone, methanol, ethanol, n-propanol, isopropanol, n-butanol, isobutanol or mixtures thereof.

The embodiment of the present invention wherein the O-methylxanthones of general formula I are preferably obtained from plant source such as *Garcinia mangostana, Garcinia cowa, Cratoxylum cochinchinense, Garcinia dulcis* or *Garcinia fusca*. The plant extract may contain one or more of the above O-methylxanthones. For example methanolic extract of the *Garcinia mangostana* fruit comprises 10-35% wt. of α-mangostin, 0.1-1% wt. of β-mangostin, 1-3% wt. of γ-mangostin, 0.1-1% wt. of garcinone C and 0.1-1% wt. of garcinone D.

The methanolic extract of *Garcinia cowa* contains 0.5-1.0% wt. of α-mangostin, 3-5% wt. of β-mangostin, 0.3-1% wt. of 6,7-dimethyl-γ-mangostin and 0.4-1.0% wt. of 3,6,7-trimethyl-γ-mangostin.

In a preferred embodiment, the invention provides a process for producing γ-mangostin having the purity in the range of 10% to 99% from O-methyl xanthone or mixture of O-methyl xanthones having the chemical structure corresponding to the general formula I and whose concentration or total of individual concentrations in case of a mixture is 10-99%, preferably the O-methyl xanthone is 99% α-mangostin obtained from *Garcinia mangostana*.

In one embodiment, the invention provides a process for producing γ-mangostin having the purity up to 100% from extracts comprising the O-methyl xanthone compound(s) of the general formula I, preferably 20 to 99% of α-mangostin from the extract of *Garcinia mangostana* pericarp.

In another preferred embodiment, the invention provides a process for producing extracts enriched in γ-mangostin in the range of 10% to 40% from extracts comprising 10-40% O-methyl xanthone compound(s) of the general formula I, preferably 10-40% α-mangostin from the extract of *Garcinia mangostana* pericarp.

In a further embodiment, the invention provides a process for producing extracts enriched in γ-mangostin in the range of 40% to 70% from extracts comprising the 40 to 70% O-methyl xanthone compound(s) of the general formula I, preferably 40 to 70% α-mangostin from the extract of *Garcinia mangostana* pericarp.

In yet another preferred embodiment, the invention provides a process for producing extracts enriched in γ-mangostin in the range of 70% to 95% from extracts comprising the 70 to 95% xanthone compound(s) of the general formula I, preferably 70-95% α-mangostin from the extract of *Garcinia mangostana* pericarp.

In yet another preferred embodiment, the invention provides a process for producing extracts enriched in γ-mangostin in the range of 95 to 99% from extracts comprising the 95 to 99% xanthone compound(s) of the general formula I, preferably 95-99% α-mangostin from the extract of *Garcinia mangostana* pericarp.

In a more preferred embodiment, the invention provides a process for producing γ-mangostin having more than 99% purity from an O-methyl xanthone compound(s) having the chemical structure corresponding to the general formula I, preferably 99% α-mangostin from the extract of *Garcinia mangostana* pericarp.

In a further embodiment of the process, the γ-mangostin product obtained of any of the O-demethylation reaction described above and having the γ-mangostin purity in the range of 10-95% is purified to more than 99% purity using a chromatographic column or crystallization technique or both depending upon the purity of the product.

Accordingly, the process for producing pure γ-mangostin as per the present invention is outlined as follows. The pure α-mangostin (99%) was dissolved in 1,2-dichloroethane and treated with pyridine. After 15 min stirring, the mixture was treated slowly with anhydrous $AlCl_3$ and sodium iodide as catalyst and then subjected to reflux temperature. After 2 h, the reaction mixture was poured into a mixture of ice water, 3N HCl and brine solution and extracted with THF. The organic layer was washed with brine, dried over anhydrous $Na_2SO_4$, treated with triethylamine and concentrated into syrup containing approximately 40% of total solids under vacuum and the crude mixture was poured'into ice water. The precipitate was filtered, washed with water and dried in a vacuum oven to obtain a residue containing 95% γ-mangostin. The mixture was crystallized from methylene chloride/acetone mixture to obtain 99% pure γ-mangostin.

Figure 3:
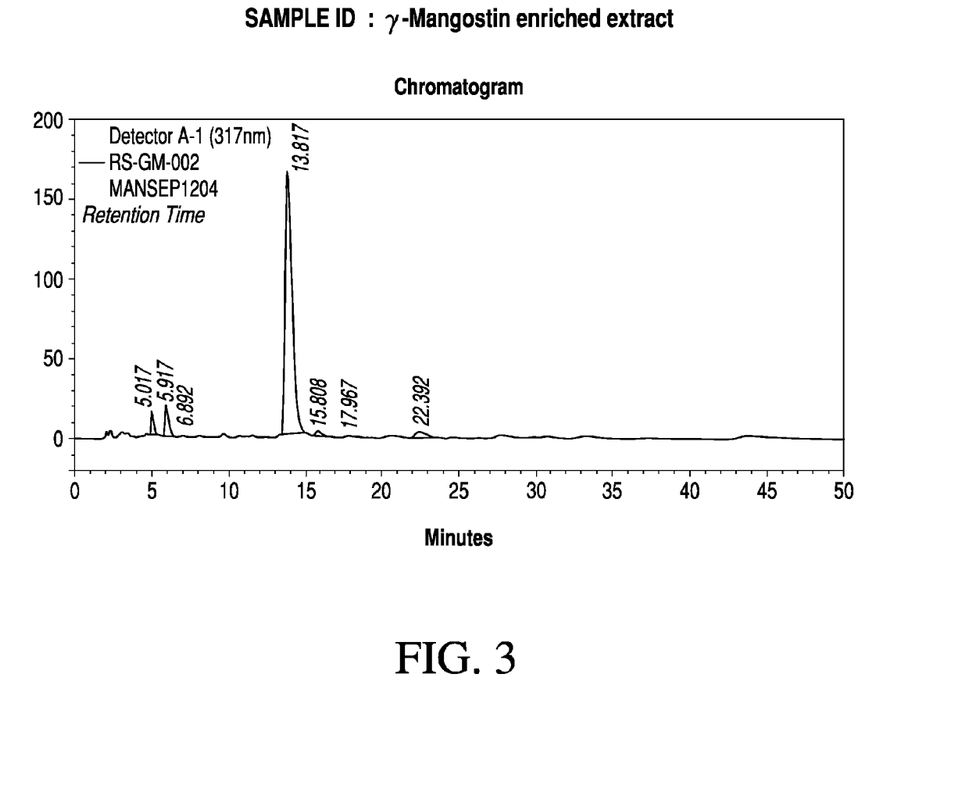
FIG. 3 presents chromatographic representation of enriched extract comprising 35% γ-mangostin obtained from the natural *Garcinia mangostana* fruit rind extract containing 34.5% α-mangostin, after demethylation using the inventive process.

In a more preferred embodiment the process for producing pure γ-mangostin or a fraction enriched in γ-mangostin comprises the steps below described for an illustrative example:

a) *G. mangostana* fruit rind was dried, ground to coarse powder and extracted with 90% methanol at 60-65° C. The solvent was removed by filtration and the extraction process repeated thrice using the same solvent and the combined solution was fine filtered and evaporated under reduced pressure. The crude extract containing 34.2% α-mangostin was dissolved in 1,2-dichloroethane and treated with pyridine. After 15 min stirring, the mixture was treated slowly with anhydrous $AlCl_3$ and sodium iodide catalyst and then subjected to reflux temperature. After 2 h, the reaction mixture was poured into a mixture of ice, 3N HCl and brine solution and mixture extracted with THF. The organic layer was washed with brine, dried over anhydrous $Na_2SO_4$, treated with triethylamine and concentrated into syrup containing around 40% total solids under vacuum and the crude mixture was poured into ice water. The precipitate was filtered, washed with water and dried in a vacuum oven to obtain a mixture containing 35% γ-mangostin. The mixture was analyzed by HPLC (FIG. 3). The composition showed 3-isomangostin in the range of 0.5-2.5%, Garcinone C in the range of 0.5-3%, Garcinone D in the range 0-0.1%, γ-Mangostin in the range of 20-40%, Deoxygartanin in the range of 0.5-1%, Gartanin in the range of 0.5-2%, α-Mangostin in the range of 0-3% as summarized in table 2.

b) dissolved the above demethylated mangostin extract enriched in γ-mangostin in a minimum quantity of 80% methanol and adjusted the pH to 10-10.5 with 5% NaOH solution and loaded on to a resin column (styrene-divinylbenzene resin, R 20). The resin was washed with 3 column volumes of water. The desired fraction was then washed with alcohol to obtain a fraction enriched with xanthones. Evaporation of the solvent from the latter fraction yielded a fraction enriched in γ-mangostin in the range of 50% to 70% by weight;

c) dispersed the said product from step b into dichloromethane, stirred the solution for 30 min and then the insoluble solid material filtered, dried the solid under vacuum to obtain a fraction comprising γ-mangostin in the range of 85% to 95% of total weight, which was then crystallized from dichloromethane/methanol mixtures to give 99% γ-mangostin.

The impure γ-mangostin obtained from demethylation reaction (step a) is alternatively subjected to normal phase silica gel/reversed phase silica flash column chromatography to yield a fraction enriched in γ-mangostin in the range of about 50 to 70%, which was then subjected to crystallization to obtain pure γ-mangostin.

Alternatively, the plant extract is purified to contain 40-70% total O-methyl xanthones having the chemical structures corresponding to the general formula I, preferably to contain 40-70% α-mangostin from the extract of *Garcinia mangostana* pericarp. The enriched extract is then subjected to demethylation reaction protocol to obtain 40-70% γ-mangostin, which is then subjected to flash chromatography or crystallization or both to obtain 99% γ-mangostin.

Alternatively, the plant extract is purified to contain 70-95% total O-methyl xanthones having the chemical structures corresponding to the general formula I, preferably to contain 70-95% α-mangostin from the extract of *Garcinia mangostana* pericarp. The enriched extract is then subjected to present inventive demethylation reaction protocol to obtain 70-95% γ-mangostin. Which is then subjected to flash chromatography or crystallization or both to obtain 99% γ-mangostin.

The demethylated reaction products having γ-mangostin in the range of 10 to 99% are subjected to chromatography or crystallization or both to yield a solid containing more than 99% of γ-mangostin.

Since, methyl ethers of γ-mangostin compounds are available plenty in plant source, many illustrative examples use methyl ethers such as α-mangostin, β-mangostin etc. However, without loss of generality, our invention covers other alkyl groups also, which may be obtained from known xanthones by synthetic methods or alkylation of γ-mangostin as described in example 19.

The present invention is illustrated by the following non-limiting examples;

EXAMPLE 1

Extraction of α-mangostin (34%) from *Garcinia mangostana* fruit: Shade dried fruit rind (1 Kg) of *G. mangostana* was pulverized to coarse powder, and extracted with 90% methanol (5 L) for 2 h at 60-65° C. The solvent was separated from the raw material by filtration. Extraction process was repeated thrice using 90% methanol (3 L+3 L+2 L). The combined extracts were fine filtered and concentrated to dryness under reduced pressure to give a residue (200 g) as a dry powder (α-Mangostin: 34.2%).

EXAMPLE 2

Preparation of 45% α-mangostin from *G. mangostana*: The 90% methanol extract of *G. mangostana* (100 g) diluted with 400 mL of water and extracted with ethyl acetate (3×500 mL) and the combined EtOAc extracts were washed with water and dried over $Na_2SO_4$. The EtOAc extract was concentrated under vacuum to give dry powder (40 g) containing α-mangostin in the range of 45% and γ-mangostin in the range of 5.5%

EXAMPLE 3

Preparation of 60% α-mangostin from *G. mangostana*: The 90% MeOH extract from 500 g of *G. mangostana* was concentrated and adjusted the pH to 10-10.5 with aqueous 5% NaOH solution (200 mL) and the basic solution was loaded on to a styrene-divinylbenzene resin (R-20, 1000 mL) and washed with 3 column volumes of water. The column then eluted with 4 column volumes of methanol. The methanol fractions were combined concentrated under reduced pressure to afford a dry powder (40 g) containing 60% α-mangostin.

EXAMPLE 4

Isolation of β-mangostin, 6,7-O-dimethyl γ-mangostin and 3,6,7-O-trimethyl γ-mangostin from *Garcinia* cowa: Shade dried fruit rind (1 Kg) of *Garcinia* cowa was pulverized to coarse powder, and extracted with 90% methanol (5 L) for 2 h at 60-65° C. The solvent was separated from the raw material by filtration. Extraction process was repeated thrice using 90% methanol (3 L+3 L+2 L). The combined methanol extracts were fine filtered and concentrated to dryness under reduced pressure to give a residue (200 g) as a dry powder. The HPLC analysis showed α-mangostin: 0.7%, β-mangostin: 4.1%, 6,7-dimethyl-γ-mangostin: 0.4% and 3,6,7-trimethyl-γ-mangostin: 0.6%.

Purification: The repeated purification of the residue by column chromatography over silica gel using hexane:ethyl acetate mixtures as eluants and monitoring by TLC yielded β-mangostin, 6,7-di-O-methyl γ-mangostin and 3,6,7-tri-O-methyl γ-mangostin as yellow solids.

β-Mangostin: Melting point: 166-170° C.; $^1$H NMR (CDCl$_3$): δ 13.41 (1H, s), 6.83 (1H, s), 6.34 (1H, s), 6.26 (1H, br s), 5.25 (2H, m), 4.10 (2H, d, J=6.4 Hz), 3.91 (3H, s), 3.81 (3H, s), 3.36 (2H, d, J=7.2 Hz), 1.83 (3H, s), 1.80 (3H, s), 1.69 (3H, d, J=1.2 Hz), 1.68 (3H, d, J=0.8 Hz); $^{13}$C NMR (CDCl$_3$): δ 181.95, 163.57, 159.86, 155.76, 155.28, 154.38, 142.63, 137.08, 131.98, 131.55, 123.21, 122.37, 112.51, 111.63, 103.90, 101.43, 88.81, 62.03, 55.79, 26.55, 25.75, 21.37, 18.17, 17.72; LC-MS (negative ion mode): m/z 423 (M–H)$^-$.

6,7-Di-O-methyl γ-mangostin: Melting point: 94-98° C.; $^1$H NMR (CDCl$_3$): δ 13.84 (1H, s), 6.73 (1H, s), 6.28 (1H, s), 6.17 (1H, br s), 5.29 (1H, t, J=7.2 Hz), 5.25 (1H, t, J=6.8 Hz), 4.13 (2H, d, J=6.4 Hz), 3.95 (3H, s), 3.79 (3H, s), 3.46 (2H, d, J=7.2 Hz), 1.84 (6H, s), 1.77 (3H, s); 1.68 (3H, s); $^{13}$C NMR (CDCl$_3$): δ 182.16, 161.56, 160.76, 158.22, 155.51, 155.13, 144.16, 137.39, 135.72, 131.77, 123.31, 121.54, 112.03, 108.53, 103.87, 98.39, 93.18, 60.95, 56.03, 26.23, 25.88, 25.82, 21.52, 18.19, 17.92; LC-MS (negative ion mode): m/z 423 (M–H)$^-$.

3,6,7-tri-O-methyl γ-mangostin: Melting point: 116-118° C.; $^1$H NMR (CDCl$_3$): δ 13.45 (1H, s), 6.74 (1H, s), 6.32 (1H, s), 5.23 (2H, m), 4.14 (2H, d, J=6.8 Hz), 3.96 (3H, s), 3.90 (3H, s), 3.76 (3H, s), 3.36 (2H, d, J=7.2 Hz), 1.85 (3H, s), 1.80 (3H, s), 1.68 (6H, s); LC-MS (positive ion mode): m/z 439 (M+H)$^+$.

EXAMPLE 5

Demethylation of α-mangostin using HBr and H$_2$SO$_4$: The α-mangostin (1 g) dissolved in acetic acid (3 mL) was treated with hydrobromic acid (48%, 6 mL) at room temperature and then heated to 90-100° C. and maintained the temperature for 2 h. The reaction mixture was poured into ice water and the mixture was extracted with EtOAc (3×50 mL). The combined organic layer was washed with saturated NaHCO$_3$ solution followed by brine and dried over Na$_2$SO$_4$. The solvent was evaporated and the residue was subjected to column chromatography over silica gel using hexane/ethyl acetate mixtures. The fractions were separated and evaporated to obtain 1,6-dihydroxy-6',6'-dimethyldihydropyrano (2',3':3,2)-6",6"-dimethyldihydropyrano (2",3":7,8)xanthone (8, 200 mg, 21%), 1,6-dihydroxy-7-methoxy-8-(3-methyl-but-2-only)-6',6'-dimethyldihydropyrano-(2',3':3,2)xanthone (9, 150 mg, 15%) and 1,6-dihydroxy-8-(3-bromo-3-methylbutyl)-7-methoxy-6',6'-dimethyldihydropyrano(2',3':3,2)-xanthone (10, 190 mg, 16%). Similarly, the same procedure was repeated with H$_2$SO$_4$ and the products were separated and identified as dimethyldihydropyrano xanthones 8 (24%) and 9 (10%).

EXAMPLE 6

Demethylation of α-mangostin using AlCl$_3$: The α-mangostin (1 g) was dissolved in 1,2-dichloroethane (15 mL) and the mixture treated slowly under vigorous stirring with AlCl$_3$ (1.3 g) and the stirring continued. After 3 h, the mixture was poured into ice water. The mixture was acidified with 3 N HCl and then extracted with ethyl acetate (3×50 mL). The combined organic layer was washed with brine and dried over Na$_2$SO$_4$. The solvent was evaporated and the residue was subjected to column chromatography over silica gel using hexane/ethyl acetate mixtures. Identical fractions were combined and evaporated to obtain 1,6-dihydroxy-7-methoxy-8-(3-methyl-but-2-only)-6',6'-dimethyldihydropyrano-(2',3':3,2)xanthone (9, 0.5 g, 50%).

EXAMPLE 7

Demethylation of α-mangostin using AlCl$_3$ at elevated temperature: A similar reaction described in example 6 was conducted with 1 g of α-mangostin, however at reflux temperature (80° C.) and the reaction worked up and purified in a similar fashion described above to give the cyclized products 8 (260 mg, 27%) and 9 (70 mg, 7%).

EXAMPLE 8

Demethylation of α-mangostin using. AlCl$_3$/N,N-dimethylaniline (U.S. Pat. No. 7,253,324 B1, dated Aug. 7, 2007): Anhydrous aluminum chloride (3.3 g) was added slowly under stirring at room temperature to N,N-dimethylaniline (3.02 mL). After the addition is complete dry toluene (10 mL) was added to the mixture and stirred for 15 min. The toluene (20 mL) solution of α-mangostin (5 g) was added to the above mixture under stirring and mixture heated at 100-110° C. for 2-3 h. After completion of the reaction, the mixture was cooled to room temperature and slowly poured into ice water with vigorous stirring and the mixture was acidified with 3N HCl to pH 1-2. The toluene layer was separated and the aqueous layer extracted twice with ethyl acetate. The combined organic layer was extracted 10% aqueous sodium hydroxide (30 mL) and the basic phase acidified with 5N HCl and extracted thrice with ethyl acetate (3×50 mL). The combined ethyl acetate layer was washed with water and brine, dried over anhydrous sodium sulfate, filtered and the solvent stripped off under vacuum to obtain a residue (6 g). The residue was subjected to column chromatography over silica gel using hexane/ethyl acetate mixtures to obtain cyclized product (8, 2.5 g, 52%), and an unexpected substitution product 11 (200 mg, 3%).

EXAMPLE 9

Demethylation of α-mangostin using AlCl$_3$/pyridine: An ice cold solution of α-mangostin (1 g) in 1,2-dichloroethane (15 mL) was treated first with anhydrous AlCl$_3$ (1.3 g). After stirring the mixture for 15 min, pyridine (2.94 mL) is added drop wise to the reaction mixture under brisk stirring while maintaining the temperature at 30-35° C. After the addition was complete the mixture was subjected to reflux for 4 h. After completion of the reaction, the reaction mixture is poured into ice cold dil. HCl and the mixture was extracted ethyl acetate (3×50 mL). The combined organic layer was washed with water and brine, dried over sodium sulfate and evaporated under vacuum to obtain a residue (1.2 g). Purification of the residue by column chromatography over silica gel using hexane/ethyl acetate mixtures yielded γ-mangostin (30 mg, 3%) and 1,6-dihydroxy-6',6'-dimethyldihydropyrano(2',3':3,2)-6",6"-dimethyldihydropyrano(2",3":7,8)xanthone (8, 386 mg, 40%).

EXAMPLE 10

Demethylation of α-mangostin using pyridine hydrochloride salt: A mixture of α-mangostin (200 mg) and pyridine-hydrochloride salt (230 mg) was heated at 190-200° C. for 2 h. The mixture was poured into ice water and extracted with ethyl acetate (3×30 mL). The combined organic layer was washed with water and brine, dried over sodium sulfate and evaporated under vacuum to obtain a residue. The residue was purified by column chromatography over silica gel using hexane/ethyl acetate mixtures to obtain dicyclized product 8 (120 mg, 62%).

EXAMPLE 11

Demethylation of α-mangostin using CeCl$_3$: A solution of α-mangostin (0.2 g) in CH$_3$CN (2 mL) was treated with CeCl$_3$ (0.68 g) and catalytic amount of KI (10 mg) and the mixture was heated at 85° C. for 3 h. The contents were poured into ice water and the mixture was extracted with ethyl acetate (3×30 mL). The combined organic layer was washed water and brine, dried over sodium sulfate and evaporated under vacuum. The residue was purified by column chromatography over silica gel using hexane/ethyl acetate mixtures to obtain dicyclized products 8 (85 mg, 44%) and 9 (35 mg, 17%).

EXAMPLE 12

Conversion of pure α-mangostin to pure γ-mangostin: A mixture of pure α-mangostin (99%, 5 g, 12.1 mmol) in ethylene dichloride (75 mL) was treated with pyridine (37 mL, 458 mmol). After 15 min, the mixture was treated slowly with AlCl$_3$ (8 g, 60 mmol) under vigorous stirring. Catalytic amount of sodium iodide (30 mg) was added and the reaction mixture was refluxed for 2 h. The reaction mixture was poured into mixture of ice cold 3N HCl (150 mL) and brine solution (80 mL). The mixture was extracted with THF (1×150 mL, 2×100 mL). The combined organic layer was washed with brine (100 mL) and dried over anhydrous Na$_2$SO$_4$ and treated with triethylamine (15 mL). The solution was concentrated into a syrup containing about 40% total solids under vacuum and the crude mixture was poured into ice water (100 mL). The precipitate was filtered, washed with water and dried in a vacuum oven to obtain a residue containing γ-mangostin 95%. The residue crystallized from methylene chloride/acetone mixture (95:5, 50 mL) to obtain 99% pure γ-mangostin (4.34 g, yield: 90%).

EXAMPLE 13

Preparation of 35% γ-mangostin extract: The crude G. mangostana extract (140 g) containing 34.2% α-mangostin from example 1 was dissolved in 1,2-dichloroethane (2.8 L) and the solution was then treated with pyridine (1.05 L, 13.02 mole). After 15 min stirring, the mixture was treated slowly with anhydrous AlCl$_3$ (260 g, 1.95 mole) at room temperature for 20 min, followed by catalytic amount of sodium iodide (1 g) and the reaction mixture was refluxed. After 2 h, the reaction mixture was poured into the mixture of ice cold 3N HCl (4 L) and brine solution (2 L). The mixture was extracted with THF (1×4 L, 2×3 L). The organic layer was washed with brine (2 L) and dried over anhydrous Na$_2$SO$_4$ and treated with triethylamine (0.4 L). The solution was concentrated into a syrup containing 40% total solids under vacuum and the crude mixture was poured into 4 L of ice water. The precipitate was filtered, washed with water and dried in a vacuum oven to obtain a mixture containing 35% γ-mangostin. The composition of the mixture as obtained by HPLC method of analysis was summarized in table 2.

TABLE 2

Composition of γ-mangostin enriched extract of Garcinia mangostana

| Name of the xanthone | Retention time (min) | Enriched extract (%) | Natural extract (%) |
|---|---|---|---|
| 3-Isomangostin | 5.0 | 2.0 | 0.1 |
| Garcinone C | 5.9 | 2.3 | 0.7 |
| Garcinone D | 6.9 | 0.0 | 1.1 |
| γ-Mangostin (1) | 13.8 | 35.4 | 5.1 |
| Deoxygartanin | 15.8 | 0.8 | 1.0 |
| Mangostinone D | 18.0 | 0.2 | 0.3 |
| Gartanin | 19.9 | 1.3 | 1.4 |
| α-Mangostin (2) | 22.3 | 1.0 | 34.2 |

EXAMPLE 14

G. mangostana Extract Containing 55-65% γ-mangostin:

Method I: The crude demethylated G. mangostana extract (50 g) enriched 35.4% γ-mangostin as prepared in example 13 was dissolved in a minimum amount of 80% methanol. The pH was adjusted to 10-10.5 with 5% NaOH and the mixture was loaded on to a resin column (styrene-divinylbenzene resin, R 20) and washed with 3 column volumes of water. The resin column was then washed with methanol to obtain a fraction enriched with mangostins. Evaporation of the solvent from the latter fraction yielded a fraction containing 3-isomangostin 3.5%, Garcinone C 4%, Garcinone D≈0.1%, γ-Mangostin 61.5%, Deoxygartanin 1%, Gartanin 2%, α-Mangostin 2%. The extracts containing other concentrations of γ-mangostin can be obtained by using appropriate starting material.

Method II: AlCl$_3$ (260 g, 1.95 mole) was added in small portions over a period of 20 min to a stirred mixture of crude G. mangostana extract (140 g) containing 60% of α-mangostin (as obtained in example 3) in ethylene dichloride (2.8 L) and pyridine (1.05 L, 13.02 mole) as described in example 13. Catalytic amount of sodium iodide (1 g) was added and the reaction mixture was refluxed for 2 h. Then the reaction was worked-up and the product extracted as described in the previous experiment to obtain a residue (120 gm) containing 63% γ-mangostin.

EXAMPLE 15

G. mangostana Fraction Containing 95-99% γ-mangostin:
Purification of 63% γ-mangostin to pure γ-mangostin: The γ-mangostin enriched fraction from the resin column in example 14, was dispersed in dichloromethane (250 mL) and the mixture was stirred at ambient temperature for 30 min. The insoluble solid material was filtered, washed with dichloromethane and dried under vacuum to obtain 90-95% γ-mangostin, which further crystallized in dichloromethane/methanol mixtures to obtain 99% pure γ-mangostin (15 g) as a pale yellow solid (mp 207-209° C.).

EXAMPLE 16

γ-Mangostin from 3,6,7-trimethyl-γ-mangostin: To a solution of 3,6,7-trimethyl-γ-mangostin (0.5 g, 1.14 mmol) in DMSO (LR, 20 mL) was added sodium cyanide (1.0 g, 20.5 mmol) at RT and the mixture was stirred at 190-200° C. for 6 h. The reaction mixture was allowed to ambient temperature and poured into ice cold water and extracted with a mixture of ethyl acetate and THF (1:1, 5×100 mL). The combined organic layer was washed with aqueous potassium permanganate (10%), water, brine and dried over sodium sulfate. The solution was filtered and the solvent evaporated under vacuum and the residue was chromatographed over silica gel column using chloroform-methanol mixture (95:5) as eluents to give α-mangostin (300 mg, 64%). The α-mangostin was then converted to γ-mangostin using the inventive demethylation procedure as described in example 12.

EXAMPLE 17

γ-Mangostin from β-mangostin: To a solution of β-mangostin (0.25 g, 0.58 mmol) in DMSO (LR, 15 mL) was added sodium cyanide (0.52 g, 10.61 mmol) at RT and the mixture was stirred at 190-200° C. for 6 h. The reaction mixture was allowed to cool to ambient temperature and then poured into ice water and the mixture was acidified with dil. HCl. The solution was extracted with ethyl acetate (5×50 mL). The combined ethyl acetate layer was washed with aqueous potassium permanganate (10%), water, brine and dried over sodium sulfate. The solution was filtered and treated with few drops of triethyl amine and the solvent evaporated. The residue was chromatographed over silica gel column using hexane/ethyl acetate mixture (80:20) as an eluent to give α-mangostin (90 mg, 37%). The α-mangostin was then converted to γ-mangostin using the inventive demethylation procedure as described in example 12.

EXAMPLE 18

Conversion of 6,7-di-O-methyl-γ-mangostin to γ-mangostin: To a solution of 6,7-di-O-methyl-γ-mangostin (0.5 g) in DMSO (LR, 20 mL) was added sodium cyanide (1.0 g) at RT and the mixture was stirred at 190-200° C. for 6 h. The reaction mixture was cooled to ambient temperature and poured into ice cold water. The mixture was extracted with a mixture of ethyl acetate and THF (1:1, 5×100 mL). The combined organic layer was washed with aqueous potassium permanganate (10%), water, brine and dried over sodium sulfate. The solution was filtered and the solvent evaporated. The residue was chromatographed over silica gel column using chloroform/methanol mixture (95:5) as eluent to give α-mangostin (330 mg, 68%). The α-mangostin was then converted to γ-mangostin using the inventive demethylation procedure as described in example 12.

EXAMPLE 19

Conversion of 7-O-ethyl-γ-mangostin to γ-mangostin: A mixture of 7-O-ethyl-γ-mangostin (2.5 g, 5.9 mmol) in 1,2-dichloroethane (50 mL) was treated with pyridine (18.5 mL, 229 mmol). After 15 min, the mixture was treated slowly with $AlCl_3$ (4.5 g, 33.8 mmol) under vigorous stirring. Catalytic amount of sodium iodide (30 mg) was added and the reaction mixture was refluxed for 2 h. The reaction mixture was poured into mixture of ice cold 3N HCl (100 mL) and brine solution (60 mL). The mixture was extracted with ethyl acetate (4×100 mL). The combined organic layer was washed with brine (50 mL) and dried over anhydrous $Na_2SO_4$ and filtered. The solution was treated with triethylamine (10 mL) and concentrated under vacuum. The residue was chromatographed over silica gel column using chloroform-acetone mixtures as eluent. The fractions were combined and evaporated under vacuum to obtain 99% pure γ-mangostin (1.8 g, yield: 77%).

EXAMPLE 20

In vitro Antioxidant Activity of Major Mangostins from *Garcinia mangostana*

Determination of Superoxide Radical Scavenging Activity:
Superoxide radical scavenging activity of test substances was determined by the method of McCord and Fridovich (J. Biol. Chem., 244, 6049, 1969). The assay mixture contained EDTA (6.6 mM containing 3 μg NaCN), riboflavin (2 μM), NBT (50 μM), phosphate buffer (67 mM, pH 7.8) in a final volume of 3 mL and various concentrations of test substances. The tubes were mixed well and optical densities were measured at 560 nm. The tubes were uniformly illuminated with an incandescent lamp for 15 min. and the optical densities were measured again at 560 nm. The percentage inhibition of superoxide radical generation was measured by comparing the absorbance values of control and those of the test substances. The $IC_{50}$ values were obtained from the plot drawn of the concentration (μg) verses percentage inhibition. The data are summarized in table 3.

Determination of DPPH (1,1-diphenylpicrylhydrazyl) Free Radical Scavenging Activity:
DPPH free radical scavenging activity was measured by the method of Lamaison, et al., (Pharma Acta Helv. 1991; 66:185) based on the reduction of colored methanolic solution of the DPPH. Free radical scavenging ability of each test substances added to the methanolic solution of DPPH was inversely proportional to the difference in initial and final absorption of DPPH solution at 517 mm Antioxidant activity is expressed as the 50% inhibitory concentration ($IC_{50}$). The reaction mixture contained $1×10^{-4}$ mM methanolic solution of DPPH and various concentrations of the test substances. Percentage inhibition was determined by comparing the absorbance values of test and control tubes. The $IC_{50}$ values were obtained from the plot drawn of the concentration (μg) verses percentage inhibition. The data are summarized in table 3.

TABLE 3

Antioxidant activity of *Garcinia mangostana* extract, α-Mangostin and γ-Mangostin

| S. No | Test substance | NBT method $IC_{50}$ μg/mL | DPPH method $IC_{50}$ μg/mL |
|---|---|---|---|
| 1 | *G mangostana*, MeOH extract | 40.7 | 29.3 |
| 2 | *G mangostana*, hydroalcohol extract | 30.2 | 15.6 |
| 3 | α-Mangostin | 61.8 | >100 |
| 4 | γ-Mangostin | 8.7 | 9.7 |
| 5 | Vitamin C | 123.6 | 3.7 |

EXAMPLE 21

5-Lipoxygenase Inhibitory Activity of Mangostins from *Garcinia mangostana*:
5-Lipoxygenase enzyme inhibitory activity was measured using the method of Schewe, et. al. (Adv Enzymol, Vol 58: pp 191-272, 1986), that was modified by Reddanna, et. al., (Methods of Enzymology, Vol 187: pp 268-277, 1990). The assay mixture contained 80 μM linoleic acid and sufficient amount of potato 5-lipoxygenase in 50 mM phosphate buffer (pH 6.3). The reaction was initiated by the addition of enzyme buffer mix to linoleic acid and the enzyme activity was monitored as the increase in absorbance at 234 nm. The reaction was monitored for 120 sec and the inhibitory potential of the test substances was measured by incubating various concentrations of test substances α-mangostin and γ-mangostin two minutes before the addition of linoleic acid. All assays were performed three times. The $IC_{50}$ values were calculated from the plot drawn of the concentrations of test substances versus percentage inhibition. The results obtained for α-mangostin and γ-mangostin are summarized in table 4.

TABLE 4

| 5-Lipoxygenase inhibitory activity | | |
| --- | --- | --- |
| S. No | Test substance | $IC_{50}$ values μg/mL |
| 1 | α-mangostin 99% | 2.7 |
| 2 | γ-mangostin 99% | 0.5 |

EXAMPLE 22

Figure 4:
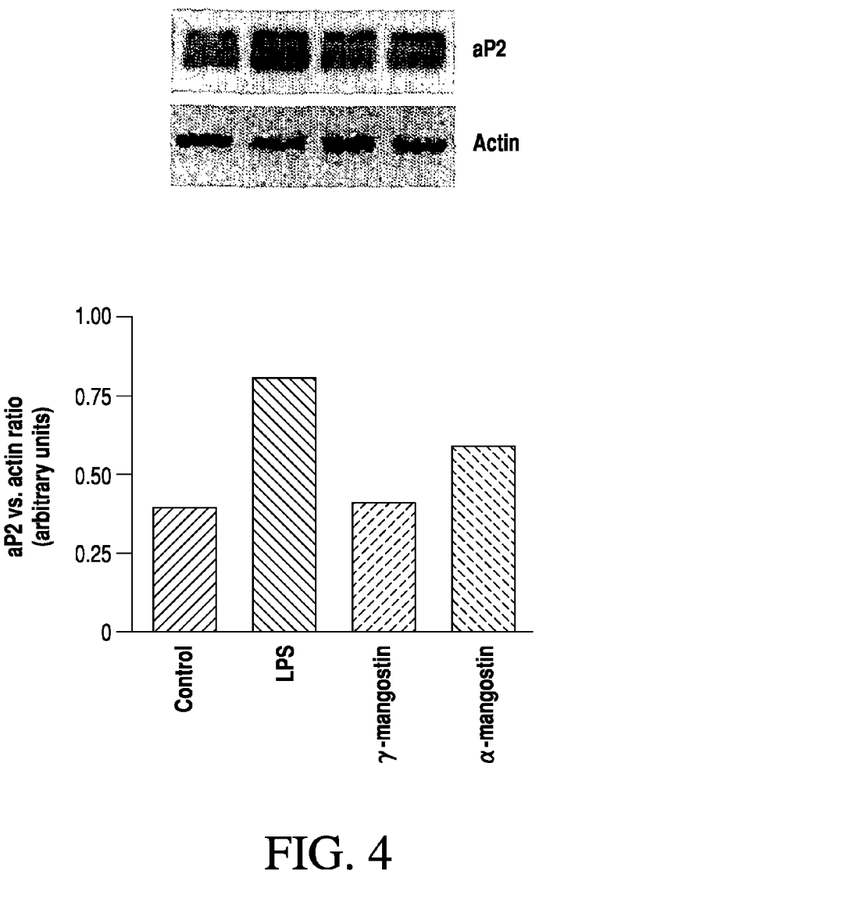
FIG. 4 shows the anti-asthma activity of mangostin compounds. The Western-immunoblots normalized with the expression of actin, depicting the modulation of expression of adipocyte fatty acid-binding protein (aP2) protein by γ-mangostin or α-mangostin in human monocytes THP-1 cells derived macrophages.

Down-regulation of aP2 protein expression by γ-mangostin and α-mangostin in human monocytes-macrophage cells:

Down-regulation of aP2 protein expression by γ-mangostin and α-mangostin was evaluated in a cell based in vitro model. Briefly, equal number of THP-1 monocyte cells were plated in 40 mm tissue culture petri-dishes and the cells were differentiated to macrophages by treatment with 10 nM Phorbol myristate acetate (PMA) for 24 h. The attached cells in the culture dishes were washed with serum free and phenol red free DMEM; and the differentiated macrophage cells were pre-treated for 2 h with 5 μg/ml of either γ-mangostin or α-mangostin or 0.1% DMSO in serum free DMEM supplemented with 2% BSA. Thereafter, the cells were primed with 100 ng/ml of LPS for 16 h to induce the inflammatory response. The 0.1% DMSO treated cells without LPS treatment were considered as vehicle control. The cellular proteins were extracted by cell lysis buffer (50 mM Tris-HCl, pH 7.5, 150 mM NaCl, 1% Triton X-100, Sodium deoxycholate 0.5%, and a protease inhibitor cocktail). The protein content was measured by Coomassie blue based Bradford method and equal amount of cellular protein lysates (2 μg) was resolved in 15% SDS-Polyacrylamide gels. The resolved proteins were electro-blotted onto nitrocellulose membranes and probed with 1:2000 dilution of anti-aP2 antibody (R&D Systems, USA), overnight. The aP2 protein expression was specifically detected by chemiluminescent substrate (Pierce, USA); detection of chemiluminescent bands and densitometric analyses were carried out on Kodak 4000 MM image station (supplied by Kodak, USA). The same nitrocellulose blots were stripped and re-probed with anti-actin antibody (Sigma Chemical CO, USA) and actin protein expression was recorded as an indication of equal protein loading in each, lane. The aP2 protein expression was normalized with the actin expression in respective samples. FIG. 4 represents immuno-western blot showing inhibition of aP2 protein expression by α- and γ-mangostin in LPS induced THP-1 human monocyte derived macrophage cells. The γ-mangostin was found to be more potent inhibitor of aP2 in vitro compared to α-mangostin.

EXAMPLE 23

A Comparative in vivo Anti-inflammatory Study of α-mangostin and γ-mangostin The anti-inflammatory efficacies of α-mangostin and γ-mangostin were evaluated by an in vivo study in Freund Complete Adjuvant induced arthritis model of Sprague Dawley rats. The rats of either sex were randomly selected and divided into three groups containing five animals in each group. The treatment group rats were supplemented with 25 mg/kg body weight of α-mangostin or γ-mangostin, or prednisolone (10 mg/kg body weight) for 14 days. The animals of control group received similar volume of 1% CMC only. At the 14 th day, Freund Complete Adjuvant (FCA) was injected subcutaneously in the sub-plantar region of the left hind paw of each animal. At the end of experiment, the animals were sacrificed and liver tissue samples were excised and stored in aliquot at −80° C. Blood samples were collected from each animal at a regular interval and paw volumes were measured by Plethysmography equipment at the day of FCA injection and after 13 days of FCA inoculation. The difference in volume of edema at the day of FCA injection and at $13^{th}$ day after induction is considered as the inflammatory response. The in vivo anti-inflammatory response of α-mangostin, γ-mangostin and prednisolone was estimated by calculating the percentage of inhibition of paw edema when compared with the CMC supplemented control.

Figure 5:
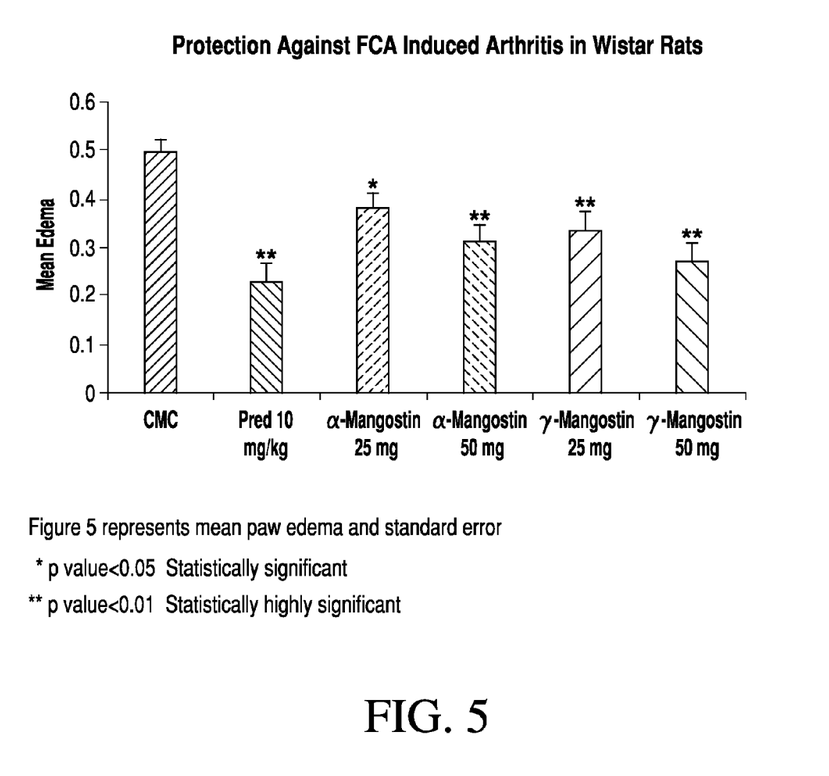
FIG. 5 shows comparison of anti-inflammatory activity of γ-mangostin and α-mangostin in Freund Complete Adjuvant induced arthritis model of Sprague Dawley rats. The bars represent the percent inhibition of paw volumes in treatment groups supplemented with γ-mangostin and α-mangostin when compared with the CMC supplemented control group. Prednisolone was used as positive control.

The γ-mangostin and α-mangostin supplemented treatment groups achieved 23% and 37% inhibition in paw edema respectively compared to 54% inhibition exhibited by prednisolone treated positive control group as shown in FIG. 5. Therefore, these data shows that γ-mangostin is relatively more potent as an anti-inflammatory agent compared to α-mangostin.

We claim:
1. A process for producing γ-mangostin from at least one O-methyl xanthone of general formula I, wherein each of $R_1$, $R_2$, $R_3$, and $R_4$ is either H or $CH_3$, with the proviso that at least one of $R_1$, $R_2$, $R_3$, and $R_4$ is $CH_3$;

General Formula I said process comprising the steps of:
(i) subjecting said at least one O-methyl xanthone to a demethylation reaction using a demethylating reagent, and
(ii) purifying the said reaction product to obtain pure γ-mangostin;
wherein the demethylating reagent comprises an organic base and a Lewis acid.
2. The process as claimed in claim 1, wherein said Lewis acid is selected from the group consisting of aluminum chloride, aluminum bromide, aluminum iodide, boron tribromide, boron trichloride-methyl sulfide complex, boron trichloride, boron trifluoride, zinc chloride and iron chloride.

3. The process as claimed in claim 1, wherein the demethylating reagent is used with a catalyst, said catalyst being:
   a metal iodide selected from the group consisting of sodium iodide, potassium iodide, magnesium iodide, calcium iodide; or
   a phase transfer catalyst.

4. The process as claimed in claim 1, wherein said organic base is selected from the group consisting of pyridine, triethylamine, N,N-diethylaniline, and N, N-dimethylaniline.

5. A process for producing γ-mangostin as claimed in claim 1, comprising the steps of:
   Step 1: preparation of pure O-methyl xanthone, semi pure O-methyl xanthone or mixtures of O-methyl xanthones of the general formula I, from a plant source selected from the group consisting of *Garcinia mangostana, Garcinia cowa, Garcinia dulcis, Garcinia fusca, Garcinia speciosa, Hydnocarpus species, Cratoxylum formosum, Allanblackia monticola, Cratoxylurn cochinchinense*, and mixtures thereof;
   Step 2: dissolving said pure O-methyl xanthone, said semi pure O-methyl xanthone or said mixtures of O-methyl xanthones of the general formula I in an organic solvent to produce a solution;
   Step 3: treating the solution with an organic base and stabilizing the solution for a suitable period of time;
   Step 4: subsequent to step (3), treating the solution with a Lewis acid and optionally with a catalyst at room temperature to produce a reaction mixture, followed by refluxing the reaction mixture for a suitable period of time, until said pure O-methyl xanthone, said semi pure O-methyl xanthone or said mixtures of O-methyl xanthones are converted to γ-mangostin;
   Step 5: quenching the reaction by pouring the reaction mixture into a mixture of ice water, an acid, and brine;
   Step 6: extracting the said acidified reaction mixture with an organic solvent; and
   Step 7: adding an organic base, to the organic layer prior to evaporating the solvent under vacuum to yield γ-mangostin.

6. The process as claimed in claim 5, wherein said Lewis acid in step 4 is selected from the group consisting of aluminum chloride, aluminum bromide, aluminum iodide, boron tribromide, boron trichloride-methyl sulfide complex, boron trichloride, boron trifluoride, zinc chloride or iron chloride.

7. The process as claimed in claim 5, wherein the catalyst is a metal iodide selected from the group consisting of sodium iodide, potassium iodide, magnesium iodide, calcium iodide or a phase transfer catalyst like tetrabutylammonium bromide.

8. The process as claimed in claim 5, wherein said organic solvent used in step 2 is selected from the group consisting of dichloromethane, dichloroethane, or ethyl acetate.

9. The process as claimed in claim 5, wherein said organic base used in step 3 is selected from the group consisting of pyridine, triethylamine, N,N-diethylaniline, and N,N-dimethylaniline.

10. The process as claimed in claim 5, wherein said organic base used in step 7 is selected from the group consisting of pyridine, triethylamine, N,N-diethylaniline, and N,N-dimethylaniline.

11. The process as claimed in claim 5, further comprising purifying γ-mangostin by subjecting the γ-mangostin to column chromatography on a solid support;
   wherein the solid support for column chromatography is selected from the group consisting of silica gel, reversed phase silica gel, styrene-divinylbenzene resin, R20 resin or anion exchange resin.

12. A process for producing γ-mangostin as claimed in claim 1, wherein:
   a) said at least one O-methyl xanthone is a mixture comprising 10-40% by wt. of α-mangostin, 0.5-2% by wt. of β-mangostin and 0.1-0.5% by wt. of γ-mangostin;
   b) said step (i) comprises demethylating said at least one O-methyl xanthone to produce a product containing 10-40% by wt. of γ-mangostin; and
   c) said step (ii) comprises purifying said product by at least one of chromatography and crystallization to produce γ-mangostin having a purity of 90-99% by wt.

13. A process for producing γ-mangostin as in claim 1, wherein:
   a) said at least one O-methyl xanthone comprise 40-70% by wt. of α-mangostin;
   b) said step (i) comprises demethylating said at least one O-methyl xanthone to produce a product containing 40-70% by wt. of γ-mangostin; and
   c) said step (ii) comprises purifying said product by at least one of chromatography and crystallization to produce γ-mangostin having a purity of 90-99% by wt.

14. A process for producing γ-mangostin as in claim 1, wherein:
   a) said at least one O-methyl xanthone comprise 70-95% by wt. of α-mangostin;
   b) said step (i) comprises demethylating said at least one O-methyl xanthone to produce a product containing 70-95% by wt. of γ-mangostin; and
   c) said step (ii) comprises purifying said product by at least one of chromatography and crystallization to produce γ-mangostin having a purity of 90-99% by wt.

15. A process for producing γ-mangostin as in claim 1, wherein:
   a) said at least one O-methyl xanthone comprise 95-99% by wt. of α-mangostin;
   b) said step (i) comprises demethylating said at least one O-methyl xanthone to produce a product containing 95-99% by wt. of γ-mangostin; and
   c) said step (ii) comprises purifying said product by at least one of chromatography and crystallization to produce γ-mangostin having a purity of 99% by wt.

16. A process for producing γ-mangostin as in claim 1, wherein:
   a) said at least one O-methyl xanthone comprise 99% by wt. of α-mangostin;
   b) said step (i) comprises demethylating said at least one O-methyl xanthone to produce a product containing more than 99% by wt. of γ-mangostin.

17. A process for producing γ-mangostin, from at least one O-methyl xanthone other than α-mangostin, wherein said at least one O-methyl xanthone is first converted to α-mangostin by a first demethylating reagent and the α-mangostin so obtained is then demethylated using a second demethylating agent comprising an organic base and a Lewis acid to obtain γ-mangostin.

18. A process as claimed in claim 17, wherein the first demethylating reagent for producing α-mangostin is sodium cyanide in dimethylsulfoxide.

19. A process for producing γ-mangostin from at least one O-methylxanthone of general formula I, wherein each of $R_1$, $R_2$, $R_3$, and $R_4$ is either H or $CH_3$, wherein a) at least one of $R_1$, $R_2$, $R_3$, and $R_4$ is $CH_3$, and b) said at least one O-methylxanthone is not α-mangostin;

General Formula I said method comprising:
demethylating said at least one O-methylxanthone with a first demethylating agent to produce α-mangostin; and
demethylating said α-mangostin with a second demethylating agent to produce γ-mangostin, said second demethylating agent comprising an organic base and a Lewis acid.

20. A process for producing γ-mangostin as claimed in claim 19, wherein said at least one O-methyl xanthone comprises a compound selected from the group consisting of; 1,6-dihydroxy-3,7-dimethoxy-2,8-bis-(3-methyl-but-2-enyl)-xanthen-9-one (β-mangostin, $R_1=R_3=H$, $R_2=R_4=CH_3$); 1,3-dihydroxy-6,7-dimethoxy-2,8-bis-(3-methyl-but-2-enyl)-xanthen-9-one ($R_1=R_2=H$, $R_3=R_4=CH_3$); 1-hydroxy-3,6,7-trimethoxy-2,8-bis-(3-methyl-but-2-enyl)-xanthen-9-one ($R_1=H$, $R_2=R_3=R_4=CH_3$); and mixtures thereof.

21. A process for producing γ-mangostin as claimed in claim 19, wherein said at least one O-methyl xanthone is derived from a plant selected from *Garcinia mangostana*, *Garcinia* cowa, *Garcinia* dulcis, *Garcinia* fusca, *Garcinia* speciosa, *Hydnocarpus* species, *Cratoxylum formosum*, *Allanblackia* monticola, *Cratoxylum cochinchinense*.

22. A process for producing γ-mangostin as claimed in claim 19 wherein said at least one O-methyl xanthone, is of semisynthetic origin obtained from xanthones isolated from a plant selected from *Garcinia mangostana*, *Garcinia* cowa, *Garcinia* dulcin, *Garcinia* fusca, *Garcinia* speciosa, *Hydnocarpus* species, *Cratoxylum formosum*, *Allanblackia* monticola, *Cratoxylum cochinchinense*.

23. A process for producing γ-mangostin as claimed in claim 19, wherein said at least one O-methyl xanthone is a pure compound or a partially pure compound obtained as a plant extract or an enriched plant extract or a mixture having the chemical structure(s) corresponding to the general formula I.

24. A process for producing γ-mangostin as claimed in claim 19, wherein the concentration of said at least one O-methyl xanthone in the starting mixture is in the range of 5% to 99%.

25. A process for producing γ-mangostin as in claim 23, wherein the concentration of said at least one O-methyl xanthone in the starting mixture is in the range of 5% to 99%.

* * * * *